United States Patent [19]
Tang et al.

[11] Patent Number: 6,060,243
[45] Date of Patent: May 9, 2000

[54] PRIMERS FOR OBTAINING HIGHLY INFORMATIVE DNA MARKERS

[75] Inventors: Jian Qing Tang, Brossard; Serge B. Melancon, Outremont, both of Canada

[73] Assignee: Procrea BioSciences Inc., Mont-Royal, Canada

[21] Appl. No.: 08/896,095

[22] Filed: Jul. 17, 1997

[51] Int. Cl.[7] .............................. C12Q 1/68; C07H 21/02
[52] U.S. Cl. ............................................. 435/6; 536/23.1
[58] Field of Search ........................ 435/6, 91.2; 935/77, 935/78; 536/23.1

[56] References Cited

U.S. PATENT DOCUMENTS 5,576,180  11/1996  Melançon ..................................... 435/6

OTHER PUBLICATIONS

Kimpton C., et al., *Forensic Science International* 71(2):137–52, 1995).

Tang, et al., *Mammalian Genome* 6:345–349, 1995.

Jarnik M., et al., *Genomics* 36: 388–398, 1996.

*Primary Examiner*—Eggerton A. Campbell
*Attorney, Agent, or Firm*—Swabey Ogilvy Renault

[57] ABSTRACT

Disclosed is a DNA amplification primer pair for the amplification of Sextolet 900 marker, which comprises R14B/264 primer having the sequence of SEQ ID NO:1 and a primer designed from the nucleic acid sequence of Sextolet 900 marker (SEQ ID NO:2). A method for the DNA fingerprinting identification of genetically related or unrelated individuals, which comprises the steps of performing DNA amplification of genomic DNA samples collected from individuals, using the primer pair R14B/264 and Sext.900E (SEQ ID NO:1 and SEQ ID NO:3, respectively) and separating the amplified DNA segments obtained whereby Sextolet 900 marker, having a heterozigosity of at least 0.97 and comprising more than 64 alleles, is amplified and serves as DNA fingerprinting of the individuals.

19 Claims, 1 Drawing Sheet

5' CAG AGC GAG ACT CT 3'

(SEQ ID NO:1)

Fig. 1

AAAGGCAGGA TAAATGTTTG ACTTTTTTCC TTTTATTTGC CACTTTTCAA
AACAAGTATC ATAATAAACT CACTAATTTA AACATTTTGA TGTATTTTAA
TACAGGGTAG TTATTGTTCT TATTGATGCT TAAATTATCC ATCTTTGACC
AATGGGAGCC TAGTTATTTT GGTTCCCTTG ACATTTTGAC AGAAATCCAA
CGATCTTTCG ATCAATGTTT GGTAGTTTCC TTGTTTCTAG TTTATTTTGT
ACTTTTTCTT CTCCTGGTTT TAGAATTAGC CTTTTTCCTA AGGATACTCA
GTTTTTTTTT TTGACACAGT TATACATGAT GTTTATAGG TTAACTATGA
TAGAAAAGC CTTGATAGGC TTCTTTGTTA GAAGGAAAG GCCAAATATN
TTCCAGGAAT ATTGGAGGTT CAGTTCCTTG GCACAGATAG GTGGTTTTCT
CTGAAATTAA TTTGGAAAAT TCTATCAGGT GAGAGCATAT CATTGTTGTG
TTTGTAAAAA ACAATGGCCA ATAGAGATAA CAGTTTATGA AAAACCACTG
TTTTCTATAA TGAAGAAGAA GACATCTTAT CTTTGTAAAC AAAGGAGCAA
AGGAAAGTGT GATTTCAGAA CTGCTTGGTT CTATGTACTG GAGATTCAGA
TGTGGGGAGG CACTCAGAAG TGTGACTTTT GGTCTCAGCC CTGTTTGGAG
CCCTTAGCCC TAAGTCAGAG AATGTACACA ATCTACCTGG GGAGGCTGAG
CTGCCCACTG GAACAGAGG TTCTTGGGTG TTCCACTGCT CCCAAGTCAG
AATCCTGGGT CTCCTACTAA TACCTGGGCA GTTCACTTTT CTCAGGTCTC
TTTTCTTTTC TAGCAGAGCC TAGAGCAGAG TAACTACTTC AGAATGCGTT
TTGGATGAAA TGAGATGACC ACATGAGACA GCAACAACTT GTGCTCAGCT
TGGGCCCCTT (CCTTT)$_x$(CT)$_y$(CTTT)$_{0-1}$CTTTT(CTTT)$_z$(CCTTCTT
TCTTT)$_2$AGA GTCTCGCTCT G (SEQ ID NO:2)

Fig. 2

5' ATGCGTTTTGGATGAAATGAGATG 3'

(SEQ ID NO:3)

Fig. 3

PRIMERS FOR OBTAINING HIGHLY INFORMATIVE DNA MARKERS

BACKGROUND OF THE INVENTION (a) Field of the Invention

The invention relates to a new primer pair consisting of R14B/264 primer and a primer designed from Sextolet 900 marker and to a highly informative DNA marker obtained from amplification of genomic DNA with the primer pair.

(b) Description of Prior Art

The science of molecular genetics provides researchers with the tremendous opportunities to study phenomena underlying genetic diseases and individualization. Both stability and variability of biological characteristics of all living organisms are assured by transmission of the hereditary material (DNA) between generations. However, the evolution process brings about cumulative differences between individuals at various levels. Sufficient data obtained from the study of polymorphic parts of the DNA (genetic markers) in human have helped map part of the human genome, and identify genes responsible for particular diseases. In addition, genetic markers are used to differentiate between individuals at the molecular level.

The basis of DNA polymorphism derives from differences in DNA sequences inherited from each parental chromosome. DNA polymorphism could also arise from a mutation in one defined single nucleotide, an insertion or a deletion of a sequence, or from variations in the length of a stretch of short tandem repeats (STR). Polymorphic DNA markers provide information regarding the segregation pattern of parental chromosomes during the mating process and hence disclose a person's genetic identity. The informativity of a specific marker is measured by its heterozygosity (H), its polymorphic information content (PIC) and the allelic frequency of each allele. The total informativity of a marker system (where several markers may be involved) is a function of the informativity extracted from the individual markers. The higher informativity of individual markers, the more informative a marker system is.

Several methods have been developed to evaluate DNA polymorphism. Restriction fragment length polymorphism (RFLP) based on Southern Blot technique is widely used to identify DNA polymorphism related to genetic diseases, genome mapping, evolution and forensic studies. Microsatellite DNA markers revealed by this method are highly informative. However, this method requires considerable amounts of DNA and large sample sizes. In addition, relatively long analysis times are needed to obtain results and translate into high cost and increases in turn around time.

Using the polymerase chain reaction (PCR), DNA present in minute amounts of biological material can be amplified into as many copies as needed. Amplified fragments are easy to be analyzed. The application of PCR to DNA marker analysis proves to be fast, reliable and cost effective. Most markers which have thus far been analyzed by PCR are of STR polymorphism. These markers consist of more than two alleles with the exceptions of some highly informative ones where more than 35 alleles (Kimpton C., et al. *Forensic Science International* 71(2):137–52, 1995) and a heterozigosity less than 0.93 have been described. No marker with more than 40 alleles and heterozigosity greater than 0.96 has been described so far.

Marker Q900 described by Tang et al. (Tang J. Q., et al., *Mammalian Genome* 6:345–349, 1995) reportedly consisted of 23 alleles and had a heterozigosity of 0.95.

U.S. Pat. No. 5,576,180 in the name of Melancon et al. discloses a DNA amplification primer pair for the simultaneous amplification of multiple highly polymorphic genomic loci. The primer pair consists of R14B/264 and Q560mak. This primer pair allows for the identification of three (3) markers including the marker Q900. However, only 23 alleles with a heterozigosity of 0.95 have been observed using the marker Q900.

It would be highly desirable to be provided with a primer pair allowing for the amplification of a marker having a high discrimination power and heterozigosity.

It would be highly desirable to be provided with a reliable method for DNA fingerprinting identification of genetically related or unrelated individuals.

SUMMARY OF THE INVENTION

One aim of the present invention is to provide a primer pair allowing for the amplification of a marker having a high discrimination power, with a heterozigosity greater than 0.96 and comprising more than 64 alleles.

Another aim of the present invention is to provide for a DNA amplification primer pair consisting of primer R14B/264 and a primer designed from Sextolet 900 marker, which corresponds to a sequence of polymorphic loci.

In accordance with the present invention there is provided a DNA amplification primer pair for the amplification of a marker having a heterozigosity of at least 0.97 and comprising more than 64 alleles, the primer pair consisting of a first R14B/264 primer (SEQ ID NO: 1) and a second primer designed from the nucleic acid sequence of SEQ ID NO:2. The second primer may be designed from a nucleic acid sequence comprised between nucleic acids 661 and 960 of the nucleic acid sequence of SEQ ID NO:2 and is preferably the Sext.900E primer having the nucleic acid sequence of SEQ ID NO:3.

The marker amplified with the DNA amplification primer pair of the present invention is preferably Sextolet 900.

In accordance with the present invention there is provided a method for the DNA fingerprinting identification of genetically related or unrelated individuals, which comprises the steps of:

a) performing DNA amplification of DNA samples collected from individuals using a first primer R14B/264 and a second primer designed from the nucleic acid sequence of SEQ ID NO:2; and b) separating the amplified DNA samples of step a) whereby polymorphic regions of different size are amplified and serve as DNA fingerprinting of said individuals.

The second primer may be labeled either by radioactive materials or by fluorescent dyes for the purpose of separating the amplified DNA samples.

The DNA amplification of step a)mentioned above may be effected by any PCR procedures, such as regular or asymetric PCR procedures.

The DNA separating step b) mentioned above may be effected using a DNA sequencer or a gel electrophoresis procedure, such as a high resolution polyacylamide sequencing gel type electrophoresis procedure.

In accordance with the present invention, there is provided a method for the DNA fingerprinting identification of genetically related or unrelated individuals, which comprises the steps of:

a) performing DNA amplification of DNA samples collected from individuals using a first primer R14B/264 and a second primer designed from the nucleic acid sequence of SEQ ID NO:2; and b) separating the amplified DNA samples of step a) whereby polymorphic regions of different size are amplified and serve as an internal standard in genetic analyses allowing to detect samples mix up.

Also in accordance with the present invention there is provided a method for the DNA fingerprinting identification of genetically related or unrelated individuals, which comprises the steps of:

a) performing DNA amplification of DNA samples from blood collected from individuals using a first primer R14B/264 and a second primer designed from the nucleic acid sequence of SEQ ID NO:2, wherein the blood is collected as blood spots on paper; and b) separating the amplified DNA samples of step a) whereby polymorphic regions of different size are amplified and serve as DNA fingerprinting for baby individualization or identification.

Further in accordance with the present invention there is provided a kit for amplification of Sextolet 900 marker, which comprises:

a) a first primer R14B/264 having the nucleic acid sequence of SEQ ID NO:1; and b) a second primer designed from the nucleic acid sequence of SEQ ID NO:2.

The kit may further comprises:

c) typed Sextolet 900 DNAs.

For the purpose of the present invention the following terms are defined below.

The term "primer" is intended to mean any oligonucleotide which can be used to direct DNA polymerization, more specifically the DNA amplification primer of the present invention consists in R14B/264 (SEQ ID NO:1) and a primer designed from Sextolet 900 marker (SEQ ID NO:2).

The expression "primer designed from Sextolet 900 marker" is intended to mean any primer suitable to be used with primer R14B/264 and which allows for the amplification of a marker having a high discrimination power, with a heterozigosity greater than 0.97 and comprising more than 64 alleles, such as primer Sext.900E (SEQ ID NO:3), without limitation.

The term "marker" is intended to mean any polymorphic genomic locus, which may vary among individuals and serve as a DNA fingerprinting identification mean.

The term "asymmetric PCR" is intended to mean any DNA amplification reaction using unequal concentration of primers.

BRIEF DESCRIPTION OF THE DRAWINGS

FIG. 1 illustrates the nucleic acid sequence of the primer R14B/264 (SEQ ID NO:1);

FIG. 2 illustrates the complete nucleic acid sequence of Sextolet 900 marker (SEQ ID NO:2); and FIG. 3 illustrates a nucleic acid sequence (SEQ ID NO:3) of a primer designed from the sequence of the Sextolet 900 marker (SEQ ID NO:2).

DETAILED DESCRIPTION OF THE INVENTION

In accordance with the present invention, there is provided a new primer pair consisting of R14B/264 (FIG. 1; SEQ ID NO:1) and a primer designed from the nucleic acid sequence Sextolet 900 marker (FIG. 2; SEQ ID NO:2). Preferably, the primer pair consists of R14B/264 and Sext.900E primers having respectively the following sequences:

R14B/264 5' CAG AGC GAG ACT CT 3' (SEQ ID NO:1) and

Sext.900E 5' ATG CGT TTT GGA TGA AAT GAG ATG 3' (SEQ ID NO:3)

Sequencing Sextolet 900 Marker and Designing the Sext.900E Primer

Marker Q900 has been amplified by polymerase chain reaction (PCR) using primers R14B/264 and Q560mak (both from U.S. Pat. No. 5,576,180). Direct sequencing of one amplified band revealed a short sequence. A new primer, designated as Q900B, was designed from this short sequence and used to amplify the same marker with an improved efficiency. The amplification products with Q900B were cloned into a plasmid vector. The clone containing the amplification product was named Q900B3.2, and was further sequenced.

The complete sequence of the non-polymorphic part of the clone Q900B3.2 revealed a 960 base pairs DNA sequence (FIG. 2; SEQ ID NO:2), differing from the sequence described by Tang et al. (Tang J. Q., et al., *Mammalian Genome* 6:345–349, 1995). In addition, different primers designed from the sequence of Sextolet 900 marker (FIG. 2; SEQ ID NO:2) have been tested. These primers combined with the 5' primer R14B/264 (from U.S. Pat. No. 5,576,180) were able to amplify the same DNA patterns using samples from genetically related and non-related individuals. Using somatic rodent-human hybrid panels (Bios Laboratories), the chromosomal location of the Sextolet 900 marker, amplified by one of the designed primers, hereinafter referred to as Sext.900E (FIG. 3; SEQ ID NO:3), has been mapped to chromosome 19, the same chromosome as the one marker Q900 was assigned to.

Polymorphic parts of 19 alleles of the Sextolet 900 marker were further sequenced. The data obtained from circling sequencing of these alleles revealed four types of variable repeats combined with few conserved nucleotides (FIG. 2). These repeats are (CCTTT)x, (CT)y, (CTTT)$_{0-1}$, and (CTTT)z. The length of the marker ranges from about 230 bp (allele 1) to >350 bp (allele 64).

The initial analysis protocol used $^{32}$P end-labeled primers (Sext.900 series) and primer R14B/264 in an asymmetric PCR. In this protocol, the concentration of Sext.900E was preferably 1 $\mu$M and R14B/264, 0.5 $\mu$M. The asymmetric PCR and labeled Sext.900E optimize the amplification of Sextolet 900 while the amplification with R14B/264 is inhibited and invisible (Tang J. Q., et al., *Mammalian Genome* 6:345–349, 1995). A protocol using a fluorescent labeled Sext.900E in which the amplification products are determined using an automatic DNA sequencer has also been developed. The amplified products were analyzed directly with the program. This fluorescent-label protocol allows for a direct identification of each individual allele.

With the current separation method used, 64 alleles have been identified using the Sextolet 900 marker in a pilot population of 180 chromosomes. Some of these alleles have between four (4) and five (5) bp while many of them have only a one (1) bp difference in length. A discrimination power and a heterozigosity value higher than 0.97 was reached within the pilot population (See table 1). The most frequent allele is about 0.0787. The number of alleles and the level of heterozigosity is expected to rise, as additional chromosomes in a larger population are analyzed.

TABLE 1

| Alleles | Frequency |
|---|---|
| A1–A7, A9–A10, A12, A14, A16, A23, A31, A39, A47–A50, A55–A56, A59–A64 | 0.56% |
| A8, A11, A13, A15, A40, A44–A45, A51–A54, A57–A58 | 1.12% |
| A17–A18, A34 | 2.25% |
| A19, A29, A37–A38, A41–A43, A46 | 1.69% |
| A20, A24, A27, A35 | 2.81% |
| A21–A22, A25, A32 | 3.93% |
| A26, A30, A36 | 3.37% |
| A28 | 5.62% |
| A33 | 7.87 |

The advantages of using the Sext.900 series primer and more specifically the Sext.900E for the amplification of the Sextolet 900 marker are as follow:

1) Compared with the Q900 marker described in Tang et al. (Tang J. Q., et al., *Mammalian Genome* 6:345–349, 1995), he background amplification is reduced to a minimum making the identification of the allelic fragments much easier;

2) by making use of a high resolution denaturing polyacrylamide gel electrophoresis, the resolution of the alleles of Sextolet 900 marker is greatly improved; and 3) the primer Sext.900E can be either labeled by fluorescent dye(s) or radioactivity allowing for the analysis of the marker using an automatic sequencer or conventional autoradiography.

Multiplex PCRs have also been tested with other markers developed. Independent amplifications were always achieved from each marker and no background is found so far in a multiplex of four (4) markers.

According to the present invention, this marker can be used in various ways. Due to its high discrimination power, the marker will be very useful where individualization is required, especially in forensic identification procedures and in paternity testing. It can also be used in linkage analysis where any interesting DNA sequences are tightly linked to this marker. The fact that this marker can be multiplexed with other markers greatly increases the overall performance of the identity test. The use of this marker in individualization, especially in babies will add a new possibility of personal identity whenever the marker is used along or combined with other markers. Due to its high discrimination power, the marker of the present invention can also be used as an internal control for PCR where the detection of the contamination of undesired genomic DNA source is very important for the experiments. Such use can be seen in virtually all PCR application from specific amplification of a single fragment in detection of specific mutations to one-cell-PCR or preimplantation diagnostic.

The present invention will be more readily understood by referring to the following examples which are given to illustrate the invention rather than to limit its scope.

EXAMPLE 1

Primer Pairs of the Present Invention

Using the sequence of Sextolet 900 marker, primers other than Sext.900E may be found.

Table 2 lists without limitation some of the primer pairs that may be used in accordance with the present invention.

TABLE 2

| Primer Pairs | Amplified DNA Fragment Size (bp) |
|---|---|
| R14B/264 and Sext.900E | about 230 to >380 |
| R14B/264 and Sext.900D | about 390 to >545 |
| R14B/264 and Sext.900F | about 210 to >360 |
| R14B/264 and Sext.900J | about 190 to >340 |

EXAMPLE 2

DNA Fingerprinting by Polymerase Chain Reaction

The reaction is carried out in a 2001 $\mu$l thin wall tube in a Robocycler™ (Stratagene). The reaction mixture (20$\mu$) includes 20 ng of genomic DNA, 1 unit of Taq DNA polymerase, and 0.2 mM each of four dNTPs, in 10 mM Tris-HCl, pH 9.0, 50 mM KCl, 1.5 mM $MgCl_2$, 2% formamide, 0.01% gelatin with 0.5 $\mu$M of the primer R14B/264 (5' CAG AGC GAG ACT CT 3', SEQ ID NO:1), 0.5 $\mu$M of the primer Sext.900E (5' ATG CGT TTT GGA TGA AAT GAG ATG 3', SEQ ID NO:3) and 0.5 $\mu$M of $^{32}P$ end-labeled Sext.900E. The reaction is carried out with 30 cycles at 94° C. for 30 sec., 53° C. for 45 sec., and 72° C. for 45 sec. An additional 72° C. incubation for 5 min. is performed at the end of the reaction.

Gel Electrophoresis

To the 20 $\mu$l of reaction, 10 $\mu$l of loading buffer (95% formamide 0.04% Bromophenol blue, 0.04% Xylene cyanol and 5 mM EDTA) was added. The sample was heated at 94° C. for 5 min. and immediately cooled to 4–6° C. Five to six (5–6) $\mu$l of the sample were loaded into a sequencing type gel (6% polyacrylamide:bis-acrylamide 19:1, 8M urea and 0.5×TBE). A sequence ladder (with 1 bp resolution) is always included to identify the size of the alleles. The gel was preheated and run under 1×TBE (90 mM Tris-borate pH 8.3, 2 mM EDTA) at constant power of 70W for 2–3 hrs. The gel was dried and autoradiographed at room temperature overnight.

When the method of the present invention is used to identify the biological father of a child, the DNA from this person is amplified by the method of the present invention and the DNA profile of the father, using the Sextolet 900 marker, is compared with that of the child. If the mother's DNA is available, one could achieve a paternity index (PI) from 3.71 to 178, depending on the frequency of the paternal allele, leading to a probability of paternity from 79% to 99.4% with only the Sextolet 900 marker. If the mother's DNA is not available, one could achieve a paternity index from 3.18 to 178, depending on the frequency of the paternal allele, leading to a probability of paternity from 76% to 99.4% with only the Sextolet 900 marker.

When the method of the present invention is used to identify whether two samples are from the same individual, the above mentioned method could be employed and the comparison of the allelic profiles from the two samples made. Since Sextolet 900 marker has a high discrimination power (>0.97) and theoretically more than 2,000 genotypes in the general population, the exclusion of a sample from different source is more likely to be achieved by using Sextolet 900 marker than any other PCR generated STR markers identified so far.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

We claim:

1. A DNA amplification primer pair for the amplification of a marker having a heterozygosity of at least 0.97 and comprising more than 64 alleles, said primer pair consisting of a first R14B/264 primer (SEQ ID NO: 1) and a second primer designed from the nucleic acid sequence of SEQ ID NO:2.

2. The DNA amplification primer pair of claim 1, wherein the second primer is designed from a nucleic acid sequence comprised between nucleic acids 661 and 960 of the nucleic acid sequence of SEQ ID NO:2.

3. The DNA amplification primer pair of claim 1, wherein the second primer is Sext.900E primer having the nucleic acid sequence of SEQ ID NO:3.

4. The DNA amplification primer pair of claim 1, wherein the marker is Sextolet 900.

5. A method for the DNA fingerprinting identification of genetically related or unrelated individuals, which comprises the steps of:

a) performing DNA amplification of DNA samples collected from individuals using a first primer R14B/264 and a second primer designed from the nucleic acid sequence of SEQ ID NO:2; and b) separating the amplified DNA samples of step a) whereby polymorphic regions of different size are amplified and serve as DNA fingerprinting of said individuals.

6. The method of claim 5, wherein the second primer is designed from a nucleic acid sequence comprised between nucleic acids 661 and 960 of the nucleic acid sequence of SEQ ID NO:2.

7. The method of claim 5, wherein the second primer is labeled either by radioactive materials or by fluorescent dyes.

8. The method of claim 5, wherein the second primer is Sext.900E primer having the nucleic acid sequence of SEQ ID NO:3.

9. The method of claim 5, wherein said DNA amplification of step a) is effected by PCR procedures.

10. The method claim 9, wherein the PCR procedures are asymetric PCR procedures.

11. The method of claim 5, wherein the DNA separating step b) is effected using a DNA sequencer or a gel electrophoresis procedure.

12. The method of claim 11, wherein said gel electrophoresis procedure is a high resolution polyacylamide sequencing gel type electrophoresis procedure.

13. A method for the DNA fingerprinting identification of genetically related or unrelated individuals, which comprises the steps of:

a) performing DNA amplification of DNA samples collected from individuals using a first primer R14B/264 and a second primer designed from the nucleic acid sequence of SEQ ID NO:2; and b) separating the amplified DNA samples of step a) whereby polymorphic regions of different size are amplified and serve as an internal standard in genetic analyses allowing to detect samples mix up.

14. A method for the DNA fingerprinting identification of genetically related or unrelated individuals, which comprises the steps of:

a) performing DNA amplification of DNA samples from blood collected from individuals using a first primer R14B/264 and a second primer designed from the nucleic acid sequence of SEQ ID NO:2, wherein the blood is collected as blood spots on paper; and b) separating the amplified DNA samples of step a) whereby polymorphic regions of different size are amplified and serve as DNA fingerprinting for baby individualization or identification.

15. A kit for amplification of Sextolet 900 marker, which comprises:

a) a first primer R14B/264 having the nucleic acid sequence of SEQ ID NO:1; and b) a second primer designed from the nucleic acid sequence of SEQ ID NO:2.

16. The kit of claim 15, further comprising;

c) typed Sextolet 900 DNAs.

17. The kit of claim 15, wherein the second primer is designed from a nucleic acid sequence comprised between nucleic acids 661 and 960 of the nucleic acid sequence of SEQ ID NO:2.

18. The kit of claim 15, wherein the second primer is Sext.900E primer having the nucleic acid sequence of SEQ ID NO:3.

19. The kit of claim 15, wherein the second primer is labeled either by radioactive materials or by fluorescent dyes.

* * * * *

SEQUENCE LISTING

```
(1) GENERAL INFORMATION:

(iii) NUMBER OF SEQUENCES: 3

(2) INFORMATION FOR SEQ ID NO:1:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide"

(iii) HYPOTHETICAL: NO (iv) ANTI-SENSE: NO (xi) SEQUENCE DESCRIPTION: SEQ ID NO:1:

CAGAGCGAGA CTCT                                                           14

(2) INFORMATION FOR SEQ ID NO:2:

(i) SEQUENCE CHARACTERISTICS:
         (A) LENGTH: 1018 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: NO (iv) ANTI-SENSE: NO (ix) FEATURE:
         (A) NAME/KEY: repeat_region
         (B) LOCATION: 961..992
         (C) IDENTIFICATION METHOD: experimental
         (D) OTHER INFORMATION: /rpt_type= "direct"
             /evidence= EXPERIMENTAL
             /rpt_unit= 961 .. 987

(ix) FEATURE:
         (A) NAME/KEY: repeat_unit
         (B) LOCATION: 961..965
         (D) OTHER INFORMATION: /rpt_type= "tandem"

(ix) FEATURE:
         (A) NAME/KEY: repeat_unit
         (B) LOCATION: 966..967
         (C) IDENTIFICATION METHOD: experimental
         (D) OTHER INFORMATION: /rpt_type= "tandem"
             /evidence= EXPERIMENTAL (ix) FEATURE:
         (A) NAME/KEY: repeat_unit
         (B) LOCATION: 968..971
         (C) IDENTIFICATION METHOD: experimental
         (D) OTHER INFORMATION: /rpt_type= "tandem"
             /evidence= EXPERIMENTAL (ix) FEATURE:
         (A) NAME/KEY: repeat_unit
         (B) LOCATION: 977..980
         (C) IDENTIFICATION METHOD: experimental
         (D) OTHER INFORMATION: /rpt_type= "tandem"
```

-continued

```
            /evidence= EXPERIMENTAL (ix) FEATURE:
        (A) NAME/KEY: repeat_unit
        (B) LOCATION: 981..992
        (C) IDENTIFICATION METHOD: experimental
        (D) OTHER INFORMATION: /rpt_type= "tandem"
            /evidence= EXPERIMENTAL (xi) SEQUENCE DESCRIPTION: SEQ ID NO:2:

AAAGGCAGGA TAAATGTTTG ACTTTTTTCC TTTTATTTGC CACTTTTCAA AACAAGTATC      60

ATAATAAACT CACTAATTTA AACATTTTGA TGTATTTTAA TACAGGGTAG TTATTGTTCT     120

TATTGATGCT TAAATTATCC ATCTTTGACC AATGGGAGCC TAGTTATTTT GGTTCCCTTG     180

ACATTTTGAC AGAAATCCAA CGATCTTTCG ATCAATGTTT GGTAGTTTCC TTGTTTCTAG     240

TTTATTTTGT ACTTTTTCTT CTCCTGGTTT TAGAATTAGC CTTTTTCCTA AGGATACTCA     300

GTTTTTTTTT TTGACACAGT TATACATGAT GTTTTATAGG TTAACTATGA TAGAAAAAGC     360

CTTGATAGGC TTCTTTGTTA GAAAGGAAAG GCCAAATATN TTCCAGGAAT ATTGGAGGTT     420

CAGTTCCTTG GCACAGATAG GTGGTTTTCT CTGAAATTAA TTTGGAAAAT TCTATCAGGT     480

GAGAGCATAT CATTGTTGTG TTTGTAAAAA ACAATGGCCA ATAGAGATAA CAGTTTATGA     540

AAAACCACTG TTTTCTATAA TGAAGAAGAA GACATCTTAT CTTTGTAAAC AAAGGAGCAA     600

AGGAAAGTGT GATTTCAGAA CTGCTTGGTT CTATGTACTG GAGATTCAGA TGTGGGGAGG     660

CACTCAGAAG TGTGACTTTT GGTCTCAGCC CTGTTTGGAG CCCTTAGCCC TAAGTCAGAG     720

AATGTACACA ATCTACCTGG GGAGGCTGAG CTGCCCACTG GGAACAGAGG TTCTTGGGTG     780

TTCCACTGCT CCCAAGTCAG AATCCTGGGT CTCCTACTAA TACCTGGGCA GTTCACTTTT     840

CTCAGGTCTC TTTTCTTTTC TAGCAGAGCC TAGAGCAGAG TAACTACTTC AGAATGCGTT     900

TTGGATGAAA TGAGATGACC ACATGAGACA GCAACAACTT GTGCTCAGCT TGGGCCCCTT     960

CCTTTCTCTT TCTTTTCTTT CCTTCTTTCT TTCCTTCTTT CTTTAGAGTC TCGCTCTG     1018

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (iv) ANTI-SENSE: NO (xi) SEQUENCE DESCRIPTION: SEQ ID NO:3:

ATGCGTTTTG GATGAAATGA GATG                                            24
```